United States Patent [19]
Schlawin et al.

[11] Patent Number: 6,123,073
[45] Date of Patent: *Sep. 26, 2000

[54] SWITCH OVERLAY IN A PISTON VENTILATOR

[75] Inventors: Craig Schlawin, Farmington; David B. Lura, Brooklyn Park, both of Minn.

[73] Assignee: Nellcor Puritan Bennett, Pleasanton, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/941,961

[22] Filed: Oct. 1, 1997

[51] Int. Cl.$^7$ .............................. A61M 16/00; A62B 7/00; F16K 31/02
[52] U.S. Cl. ...................................... 128/204.21; 200/512
[58] Field of Search .................. 200/51.16, 512, 200/513, 517, 518, 520, 530; 128/204.21

[56] References Cited

U.S. PATENT DOCUMENTS

| | | | |
|---|---|---|---|
| 4,626,847 | 12/1986 | Zato | 340/825.56 |
| 4,767,943 | 8/1988 | Adler et al. | 307/119 |
| 4,771,139 | 9/1988 | DeSmet | 200/5 A |
| 5,510,584 | 4/1996 | Norris | 200/5 A |
| 5,512,721 | 4/1996 | Young et al. | 200/512 |
| 5,561,278 | 10/1996 | Rutten | 200/5 A |
| 5,564,560 | 10/1996 | Minelli et al. | 200/516 |
| 5,824,978 | 10/1998 | Karasik et al. | 200/1 B |

*Primary Examiner*—John G. Weiss
*Assistant Examiner*—Joseph F. Weiss, Jr.
*Attorney, Agent, or Firm*—Hovey, Williams, Timmons & Collins

[57] ABSTRACT

A patient ventilator is connected with two stand-by switches wherein activation of both switches is required for stopping the ventilating function. The preferred stand-by switches are in the form of membrane switches in which a conductive dome is positioned and spaced between respective layers having electrical traces thereon cooperating with the dome for defining the switches. The application of manual pressure closes the spaces between the layers and activates both switches.

18 Claims, 1 Drawing Sheet

SWITCH OVERLAY IN A PISTON VENTILATOR

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention relates to the field of patient ventilators and membrane switches. More particularly, the invention is concerned with a patient ventilator connected to two stand-by switches wherein activation of both switches is required for stopping the ventilating function. The preferred stand-by switches are in the form of membrane switches in which a conductive dome is positioned and spaced between respective layers having electrical traces thereon cooperating with the dome for defining the switches. The application of manual pressure closes the spaces between the layers and activates both switches.

2. Description of the Prior Art

Patient ventilators assist or totally provide the respiratory function for a patient. If a single stand-by switch is used for stopping the ventilating function, there is a risk that a defect in the switch, such as a short circuit, could cause the ventilator to stop. The prior art solves this problem with a rotary switch mechanism having two stand-by switches in which activation of both switches is required for stopping the ventilating function. Those skilled in the art appreciate, however, that rotary switch mechanisms tend to be bulky and uneconomical, especially for the smaller sized home ventilators.

SUMMARY OF THE INVENTION

The present invention solves the prior art problems discussed above and provides a distinct advance in the state of the art. In particular, the ventilator and switch combination hereof provides a compact and economical arrangement.

In a preferred embodiment, a ventilator is connected to a membrane switch assembly having first and second membrane switches coupled with the ventilator for stopping the ventilating function thereof only upon activation of both of the switches. The assembly includes first and second membrane layers with an intermediate membrane layer therebetween. The layers are spaced and include circuit trace thereon cooperatively defining the switches in superposed relationship for activation of both switches in response to pressure closing the spaces between the layers. The preferred intermediate layer is in the form of a resilient, conductive dome positioned between the traces of the first and second layers. Pressure on the first layer causes the trace thereon to contact the top of the dome closing the first switch. This, in turn, collapses the dome into contact with the trace of a second layer thereby closing the second switch.

DETAILED DESCRIPTION OF THE PREFERRED EMBODIMENT

Figure 1:
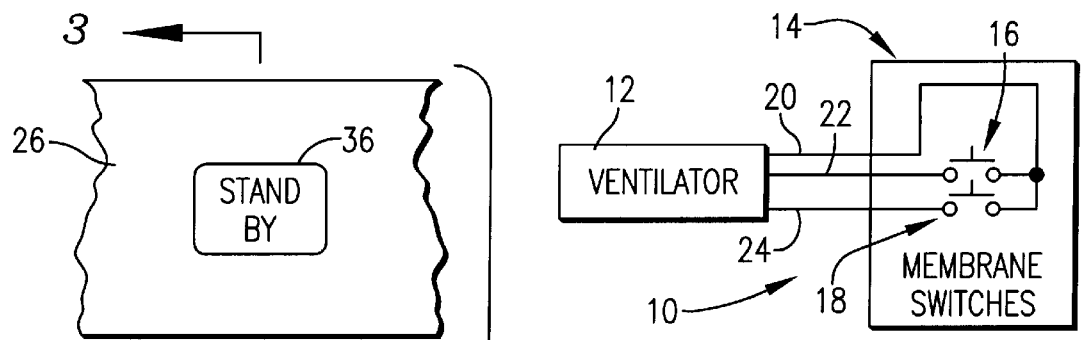
FIG. 1 is a schematic representation of a patient ventilator connected with two stand-by switches in the form of membrane switches.

FIG. 1 illustrates preferred embodiment 10 in accordance with the present invention including ventilator 12 and membrane switch assembly 14. Ventilator 12 can be any type of ventilator such as hospital ventilator or a home care ventilator. Such ventilators are used for ventilating a patient by assisting the respiration or by providing the total respiratory function.

Membrane switch assembly 14 includes normally open, parallel connected, stand-by switches 16 and 18 electrically connected to ventilator 12 by line 20, common to both switches, and lines 22 and 24 for switches 16 and 18 respectively. In one example of use, ventilator 12 is controlled by a microprocessor with line 20 providing a positive supply voltage to switches 16, 18. Lines 22 and 24 provide input to the microprocessor and both must be closed to signal the stopping of the ventilating function. This may result in the ventilator placed in a pause mode or could signal power down of the ventilator.

Figure 2:
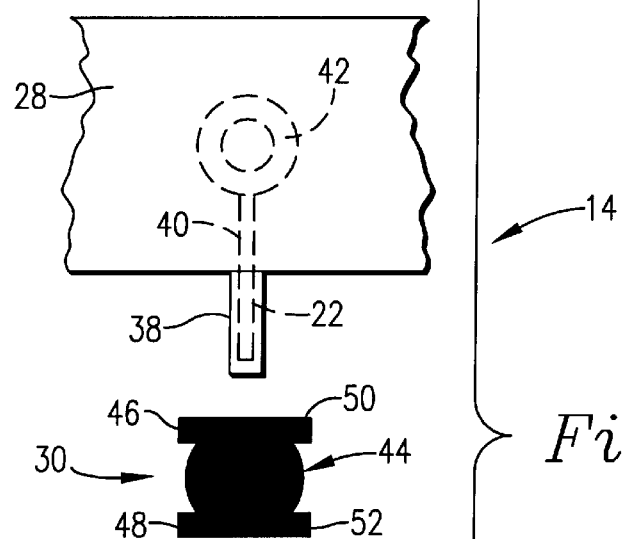
FIG. 2 is an exploded view of the components of the preferred membrane switches of FIG. 1.
Figure 2:
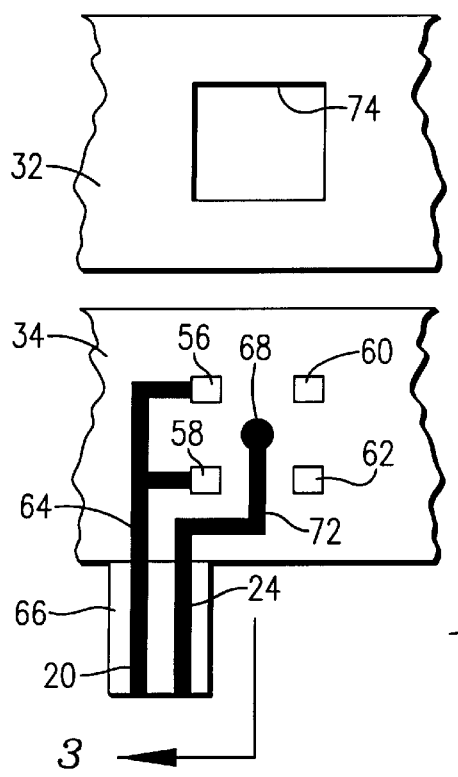
Figure 3:
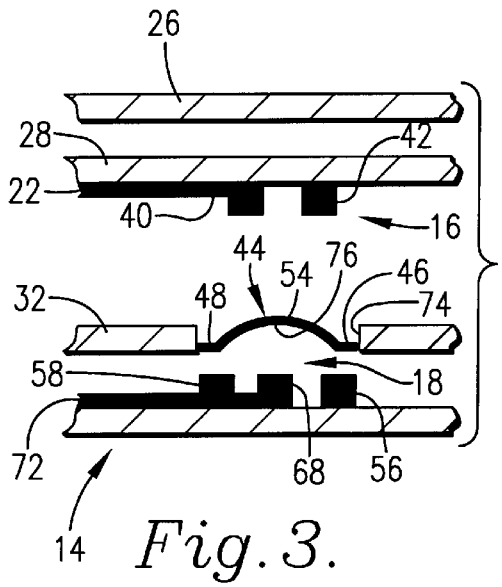
FIG. 3 is a sectional view taken along line 3—3 of FIG. 2.

FIGS. 2 and 3 further illustrate membrane switch assembly 14 which typically would include switches other than stand-by switches 16, 18 for controlling the various functions of the ventilator such as start, pressure adjustments and timing adjustments. As illustrated, assembly 14 includes a plurality of layers including graphic overlay 26, first switch layer 28, an intermediate switch layer in the nature of conductive dome 30, dome positioning layer 32, and second switch layer 34. As is conventional, layers 26, 28 and 32, 34 are composed of polyester, and adhesive is included between the various layers. Also, assembly 14 may include other layers as is conventional such as ESD grids, EMI planes, a clear window layer and so forth. Graphic overlay 26 includes graphic 36 printed thereon bearing the legend STAND-BY indicating the function of switches 16, 18.

First layer 28 includes connection tab 38 and circuit trace 40 on the lower or inboard side thereof as illustrated in FIG. 3. Circuit trace 40 includes trace portion 42 in the shape of a torus for engaging the top of dome 30 with linear portion of trace 40 being line 22 extending onto connection tab 38.

Resilient conductive dome 30 is composed of metal such as spring steel and includes dome section 44 and four, outwardly extending, electrical contacts 46, 48, 50 and 52. Upper surface 54 of dome section 44 and torus-shaped trace portion 42 of first layer 28 are spaced and define normally open, switch 16 therebetween. Contact between trace portion 42 and upper surface 54 result in closure of switch 16.

Second switch layer 34 includes electrical trace configured as contact pads 56, 58, 60 and 62 and trace portion 64 configured as common line 20 extending onto tab 66, and further includes circular trace portion 68 positioned centrally and electrically connected with trace portion 72 as line 24 extending onto tab 66 spaced from line 22. The lower surface 76 of dome section 44 and circular trace portion 68 are spaced and define normally open, switch 18 therebetween.

Dome contacts 46–52 are configured to register in electrical contact with pads 56–62 respectively. In this position, positioning layer 32 overlies second layer 34 with window 74 surrounding and locating dome 30 in the registration position relative to second layer 34. As best viewed in FIG.

3, torus-shaped trace portion 42, dome section 44 and circular trace portion 68 are in axial alignment. These components of assembly 14 are spaced so that switches 16, 18 are normally open.

In operation, the user applies pressure, that is, presses on graphic 36 of overlay 26. This action shifts first layer 28 downwardly and closes the space between torus-shaped trace portion 42 and upper surface 54 of dome section 44 to make electrical contact between these two components thereby closing switch 16.

The pressure on graphic 36 also causes torus-shaped trace portion 42 to collapse dome section 44 to close the space between lower surface 76 and circular trace portion 68. This results in electrical contact thereby closing switch 18. With both switches closed, signals are provided on both of lines 22 and 24 to ventilator 12 indicating that the ventilating function should cease. With the release of pressure on graphic 36, the layers of assembly 14 return to the spaced position and switches 16, 18 return to their respective open positions. The configuration of membrane switch assembly 14 in accordance with the present invention provides two superposed membrane switches, which has been unavailable in the prior art.

It will be appreciated that if either of switches 16 and 18 were to fail in the shorted condition, such would be insufficient to signal ventilator 12 to cease the ventilating function. It would still require pressing graphic 36 to close the other of the switches. In this way, the present invention provides reliable performance using the compactness and economies of membrane switches. Moreover, membrane switches are generally more resistant to adverse effects from environmental conditions such as moisture and dust as compared to the prior art mechanical switches.

Those skilled in the art will appreciate that the present invention encompasses many variations in the preferred embodiment described herein. Having thus described the preferred embodiment of the present invention, the following is claimed as new and desired to be secured by Letters Patent:

What is claimed is:

1. In combination:
   a respiratory ventilator for ventilating a patient; and
   a membrane switch assembly having first and second membrane switches coupled with said ventilator for stopping said ventilator only upon activation of both of said switches,
   said assembly including non-conductive first and second membrane layers with an intermediate membrane layer therebetween,
   said intermediate layer comprising a resilient conductive dome,
   each of said layers being spaced and each of said first and second layers including a circuit trace thereon cooperatively defining said switches positioned in superposed relationship for activation of both of said switches in response to a single application of pressure closing the spaces between said layers.

2. The combination as set forth in claim 1, said first layer including a circuit trace thereon defining a portion of said first switch, said second layer including a circuit trace thereon defining a portion of said second switch, said intermediate layer being electrically conductive and cooperating with said circuit trace of each of said first and second layers for defining said switches.

3. The combination as set forth in claim 2, said dome positioned between the circuit trace of each of said first and second layers so that pressure upon all of said layers brings said trace of said first layer into electrical contact with said dome and brings said trace of said second layer into electrical contact with said dome on the opposed side thereof.

4. The combination as set forth in claim 3, said switches presenting normally open switches connected in parallel.

5. The combination as set forth in claim 3, said trace of said first layer being in the form of a torus spaced and adjacent to the peak of said dome.

6. The combination as set forth in claim 5, said dome presenting outwardly extending contacts, said trace of said second layer including conductor pads in registration with said contacts of said dome.

7. The combination as set forth in claim 6, said trace of said second layer including a central portion in registration with the axis of said dome.

8. The combination as set forth in claim 1, all of said layers being resilient for returning to said spaced relationship upon removal of said pressure.

9. The combination as set forth in claim 1, said switches presenting normally open switches connected in parallel.

10. A membrane switch apparatus comprising:
    a non-conductive first membrane layer;
    a non-conductive second membrane layer; and
    a intermediate membrane layer between said first and second layers,
    said intermediate layer comprising a resilient, conductive dome,
    all of said layers being spaced and each of said first and second layers including a circuit trace thereon cooperatively defining first and second switches positioned in superposed relationship for activation of both of said switches in response to a single application of pressure closing the spaces between said layers.

11. The apparatus as set forth in claim 10, said first layer including a circuit trace thereon defining a portion of said first switch, said second layer including a circuit trace thereon defining a portion of said second switch, said intermediate layer being electrically conductive and cooperating with said circuit trace of each of said first and second layers for defining said switches.

12. The apparatus as set forth in claim 10, said dome positioned between the circuit trace of each of said first and second layers so that pressure upon all of said layers brings said trace of said first layer into electrical contact with said dome and brings said trace of said second layer into electrical contact with said dome on the opposed side thereof.

13. The apparatus as set forth in claim 12, said switches presenting normally open switches connected in parallel.

14. The apparatus as set forth in claim 12, said trace of said first layer being in the form of a torus spaced and adjacent to the peak of said dome.

15. The apparatus as set forth in claim 14, said dome presenting outwardly extending contacts, said trace of said second layer including conductor pads in registration with said contacts of said dome.

16. The apparatus as set forth in claim 15, said trace of said second layer including a central portion in registration with the axis of said dome.

17. The apparatus as set forth in claim 10, all of said layers being resilient for returning to said spaced relationship upon removal of said pressure.

18. The apparatus as set forth in claim 10, said switches presenting normally open switches connected in parallel.

* * * * *